United States Patent [19]
Park et al.

[11] Patent Number: 6,037,511
[45] Date of Patent: Mar. 14, 2000

[54] CATALYST FOR DEHYDROGENATING AROMATIC WITH CARBON DIOXIDE

[75] Inventors: Sang-Eon Park; Jong-San Chang; Yong Ki Park; Min Seok Park; Chul Wee Lee, all of Daejeon; Jermim Noh, Junjoo, all of Rep. of Korea

[73] Assignee: Korea Research Institute of Chemical Technology, Rep. of Korea

[21] Appl. No.: 09/265,359

[22] Filed: Mar. 10, 1999

Related U.S. Application Data

[62] Division of application No. 09/163,350, Sep. 30, 1998.

[51] Int. Cl.$^7$ .............................. C07C 5/32; C07C 5/327; C07C 5/333
[52] U.S. Cl. ........................... 585/440; 585/435; 585/444
[58] Field of Search ................................... 585/435, 440, 585/444

[56] References Cited

U.S. PATENT DOCUMENTS

| | | | |
|---|---|---|---|
| 2,426,829 | 9/1947 | Kearby . | |
| 3,742,079 | 6/1973 | Etherington | 585/444 |
| 4,451,686 | 5/1984 | De Clippelier et al. | 585/444 |
| 4,565,899 | 1/1986 | Burress | 585/445 |
| 4,788,371 | 11/1988 | Imai et al. | 585/443 |
| 5,023,225 | 6/1991 | Williams et al. | 502/304 |
| 5,190,906 | 3/1993 | Murakami et al. | 502/304 |

FOREIGN PATENT DOCUMENTS 201 159   8/1988   United Kingdom .

OTHER PUBLICATIONS

"Structure of the Active Layer and Catalytic Mechanism of the V$_2$O$_5$/MgO Catalysts in the Oxidative Dehydrogenation of Ethylbenzene to the Styrene", J. Hanuza et al., Journal of Molecular Catalysis, vol. 29, No. 1, Feb. 1985, pp. 109–143.

"Combination of Ethylbenzene Dehydrogenation and Carbon Dioxide Shift–Reaction Over a Sodium Oxide/Alumina Catalyst", Applied Catalysis, vol. 37, 1988, pp.207–215, No Month Available.

"An Interpretation of the High–Pressure Kinetics of Ammonia Synthesis Based on a Microscopic Model", P. Stoltze et al., Journal of Catalysis, vol. 110, No. 1, Mar. 1988, pp. 1–10.

"A Catalytic Membrane Reactor Its Performance in Comparison with Other Types of Reactors", Yi–Ming Sun et al., Industrial & Engineering Chemistry Research, vol. 29, No. 2., Feb. 1990, pp. 232–238.

"Capillary Polysulphone Membranes With Entrapped Whole Cells: Influence of Cell Loading and Filler Molecular Weight on Membrane Mechanical and Kinetic Performance", Journal of Molecular Catalysis, vol. 58, No. 2, Feb. 1, 1990, pp. 277–286.

"influence of Carbon Dioxide Addition Upon Decay of Activity of a Potassium–Promoted Iron Oxide Catalyst for Dehydrogenation of Ethylbenzene". Junshi Matsui et al., Applied Catalysis, vol. 67, No. 2, Jan. 3, 1991, pp. 179–188.

"Aromatic Compounds Synthesis from Cyclopentadiene", Akira Sato, et al., Applied Catalysis A, vol. 111, No. 1, Apr. 14, 1994, pp. 1–9.

"Oxidative Dehydrogenation of Ethylbenzene to Styrene over Carbonaceous Catalysts", Russel S. Drago et al., Applied Catalysis A, vol. 112, No. 2, May 26, 1994, pp. 117–124.

"Oxidative Dehydrogenation of Ethylbenzene with Carbon Dioxide", Mitsu–o Sugino, et al., Applied Catalysis A, vol. 121, No. 1, Jan. 5, 1995, pp. 125–137.

"Alternative Processes for the Production of Styene", F. Cavani et al., Applied Catalysis A, vol. 133, No. 2, 1995, pp. 219–239, No Month Available.

"Oxdehydrogenation of Ethlbenzene to Styrene over Metal Pyrophosphates", G. Edwin Vrieland, Journal of Catalysis, vol. 111, pp. 1–13, 1988, No Month Available.

"Roles of Potassium in Potassium–Promoted Iron Oxide Catalyst for Dehydrogenation of Ethylbenzene", Takenori Hirano, Applied Catalysis, vol. 26, 1986, pp. 65–79, No Month Available.

*Primary Examiner*—Elizabeth D. Wood
*Attorney, Agent, or Firm*—Finnegan, Henderson, Farabow, Garrett & Dunner, LLP

[57] ABSTRACT

The invention herein relates to a catalyst for enhancing the conversion of the dehydrogenation reaction of aromatic hydrocarbons such as ethylbenzene under a flow of carbon dioxide, which is expressed by the following formula I, wherein a catalyst in which an active component of iron oxides is highly dispersed onto a zeolite, activated charcoal, γ-alumina or silica carrier. Further, the invention relates to a dehydrogenation method of aromatic hydrocarbons by means of using said catalyst:

$$(Fe^{II}{}_xFe^{III}{}_yO_z)/S \qquad (I)$$

wherein S denotes a zeolite, activated charcoal, γ-alumina or silica carrier, and the initial state of iron oxide is as follows:

$$x=0.1-2 \;\; x+y=3 \text{ and } z=(2x+3y)/2$$

As compared to the case in which the reaction is carried out without carbon dioxide, the invention herein is characterized by the significant enhancement of the activity of the dehydrogenation reaction of aromatic hydrocarbons in conjunction with the catalytic stability under a flow of carbon dioxide in the reaction temperature range of 500~700° C. In particular, the invention provides a method of enhancing the dehydrogenation activity, wherein a catalyst is used, in which having a carrier such as a zeolite, active carbon, γ-alumina or silica is loaded with iron oxides containing a high concentration of Fe(II) species.

2 Claims, No Drawings

CATALYST FOR DEHYDROGENATING AROMATIC WITH CARBON DIOXIDE

This is a division of application Ser. No. 09/163,350, filed Sep. 30, 1998, which is pending.

BACKGROUND OF THE INVENTION

1. Field of the Invention

The invention herein relates to a catalyst for enhancing the conversion of the dehydrogenation reaction of aromatic hydrocarbons such as ethylbenzene, wherein carbon dioxide is used as an oxidant over a catalyst in which an active component of iron oxides is highly dispersed onto a zeolite, active carbon, γ-alumina or silica carrier. Further, the invention relates to a dehydrogenation method of aromatic hydrocarbons by means of using said catalyst.

2. Description of the Prior Art

Styrene, one of aromatic hydrocarbons, manufactured by the dehydrogenation process of ethylbenzene is a very important compound and is widely used as a raw material and a monomer for synthetic rubber, ABS resin and polystyrene. Further, due to an increase in demand, the production amount of styrene has been grown year by year. Styrene is industrially manufactured by the dehydrogenation process of ethylbenzene via excess steam over an iron oxide-based catalyst. Alternatively, it can be manufactured by the epoxidation process of propylene and ethylbenzene hydroperoxide over a molybdenum-based catalyst. Among the aforementioned methods, the typical styrene manufacturing process involves the dehydrogenation process of ethylbenzene via the addition of steam and is responsible for 90% of the world styrene production.

Based on a rapid increase in demand of synthetic rubber, the research on the subject of the dehydrogenation reaction of ethylbenzene for mass production of styrene has been actively carried out from the early 1940's in the US and other parts of the world. In the case of the dehydrogenation process of ethylbenzene, which is the most widely used styrene manufacturing process, the process is operated by adding excess steam to ethylbenzene in an adiabatic reactor under pressurized condition with the reaction temperature of about 600° C. In this process, the most widely known industrial catalyst is an iron oxide catalyst without a carrier, and the common constituents as core therein are $Fe_2O_3$ and $K_2O$. As early as 1947, in U.S. Pat. No. 2,426,829 granted to Standard Oil Co. as assignee, the activity of an iron oxide catalyst in conjunction with an alkaline promoter during the dehydrogenation process of ethylbenzene via steam vapor was shown to be most active. Further, it is known that various catalyst promoters to added to the Fe—K based catalyst contribute to the enhancement of the catalytic activity, styrene selectivity and structural stability. For example, U.S. Pat. No. 5,023,225 teaches that cerium and chromium contribute to the enhancement of the catalytic activity and suggests that calcium, vanadium, molybdenum and tungsten contribute to the enhancement of selectivity while cerium and chromium contribute to the structural stability. Further, U.S. Pat. No. 5,190,906 granted to Nissan Girdler Catalyst Co. as assignee teaches that the activity with respect to the dehydrogenation of ethylbenzene using steam vapor increases when a small amount of titanium oxide is added to the K—Fe oxide catalyst.

On the other hand, as pointed out by Cavani and Trifiro, it is known that the problems seen in the other dehydrogenation process of paraffin are also observed in the dehydrogenation process of ethylbenzene (*Appl. Catal.*, 133, 219 (1995)). The problems associated with the dehydrogenation process of ethylbenzene are as follows: thermodynamic limitation, low conversion rate, recycling of unreacted reactants, high endothermic energy ($\Delta H°=28.1$ kcal/mol), and deactivation of a catalyst by coke formation. During the industrial dehydrogenation process of ethylbenzene, an excess steam is added for proper operation, and the necessary heat for reaction is partially provided by super-heated steam. Then, the partial pressure of ethylbenzene and hydrogen is reduced, which brings about a shift in the equilibrium towards the high conversion of ethylbenzene. Further, because the modification reaction of steam concurrently occurs at this point, the amount of coke or its precursor formed on the surface of a catalyst during the dehydrogenation reaction of ethylbenzene is reduced, which in turns significantly increases the lifetime of a catalyst. However, the process is still problematic due to the following factors: an increase in cost of energy due to the use of excess steam, consumption of ethylbenzene and styrene due to the side reaction of steam reforming, and a difficulty in controlling the oxidation state of the catalyst.

Various methods have been devised to overcome several problems associated with the use of steam during the dehydrogenation of ethylbenzene. The first method involves combining the dehydrogenation of ethylbenzene and the oxidation reaction of hydrogen. In this method, the dehydrogenated hydrogen is oxidized by oxygen in order to supply the heat of reaction and to modify the reaction equilibrium as deemed necessary. The second method involves lowering the reaction temperature by means of oxidative dehydrogenation via molecular oxygen, thereby converting the endothermic reaction to one of exothermic reaction. The third method is an attempt to lower the reaction temperature by improving the reaction equilibrium of the dehydrogenation of ethylbenzene, which is an equilibrium limitation reaction, by means of application of an inorganic membrane catalyst. Lastly, the fourth method is an attempt to increase the yield of styrene and the activity of dehydrogenation of ethylbenzene by using a mild oxidant, i.e., carbon dioxide.

As mentioned above, the first method can provide a shift in the reaction equilibrium to the direction of a high yield of styrene by means of continuously removing the produced hydrogen during the reaction. In actuality, when the reactants are passed through the three types of reactors using the above method, the conversion of ethylbenzene can reach 80% or above per cycle with the styrene selectivity not far off from that of the dehydrogenation process via steam (*Appl., Catal.*, 133, 219 (1995)). In this process, two types of catalysts are mainly used. The first is the case in which a catalyst for dehydrogenation of ethylbenzene and a catalyst for hydrogen oxidation are used in two catalyst layers. The second type is the case in which one catalyst having two concurrent catalytic functions is used. U.S. Pat. No. 4,788,371 as assigned to UOP suggests the use of a catalyst containing $Sn/K/Pt/Al_2O_3$ with the capacity of simultaneous dehydrogenation and hydrogen oxidation. Based on such method which enables the selective oxidation of hydrogen in production, it was further suggested that the SMART process be used with the enhanced process of dehydrogenation of ethylbenzene (*Appl. Catal.*, 133, 219 (1995)).

In the second method of the oxidative dehydrogenation of ethylbenzene with molecular oxygen, there is an advantage in that not only the heat of reaction is exothermic ($\Delta H°=-29.7$ kcal/mol), but also the reaction equilibrium can be markedly increased. However, since the oxidative dehydrogenation uses molecular, oxygen there is a danger of explosion due to the side reaction of the complete oxidation reaction and the violent reaction of oxygen and the reactants. The key to the second method is nevertheless the high selectivity of styrene of 90% or more. In order to increase the selectivity of oxidative dehydrogenation reaction, several procedures have been tried as follows: oxidative dehydrogenation over metal oxides having weak acidity or weak, oxidative dehydrogenation with a mild oxidant instead of oxygen, and oxidative dehydrogenation with an electrochemical method. Among these procedures, Vrieland was able to obtain a styrene selectivity close to 90% by applying various metal phosphates at the reaction temperature of 500–600° C. (*J. Catal.*, 111, 1 (1988)). Drago et al. disclosed that a high styrene selectivity of 90% in conjunction with a high conversion of ethylbenzene was obtained at a low reaction temperature of 350° C. by using a carbon molecular sieve as catalyst (*J. Mol. Catal.*, 58, 227 (1990); *Appl. Catal.*, 112, 117 (1994)). Further, Hanuza et al. was able to obtain selectivity of 93.5% and conversion of 65% at 520° C. when the reaction was carried out with the molar ratio of 1:1:8:20 with respect to benzene/oxygen/steam/nitrogen over a catalyst containing 9% $V_2O_5$ (*J. Mol. Catal.*, 29, 109 (1985)).

The third method, the application of a catalytic inorganic membrane reactor, can improve the conversion of ethylbenzene by favorably shifting the reaction equilibrium by means of introducing a hydrogen permselective membrane. In particular, UK Patent No. 2,201,159 suggests the use of a ceramic membrane reactor which can effectively separate hydrogen among the dehydrogenated products. Wu and Liu were able to increase the yield of styrene by combining K-promoted $Fe_2O_3$ catalyst and inorganic membrane reactor (*Ind. Eng. Chem. Res.*, 29, 232 (1990)). The method is superb in principle but has several disadvantages as follows: the expensive construction costs of facilities, the difficult commercialization of inorganic membrane reactor, and the inefficient heat and material transfer.

Meanwhile, in addition to these aforementioned methods, the dehydrogenation of ethylbenzene using carbon dioxide has been mentioned in the recent years. Carbon dioxide possesses a much weak oxidizability as compared to oxygen molecule but can nevertheless be used as a mild oxidant. In some cases, by using a mild oxidizability of carbon dioxide, the activity and selectivity can be markedly improved. However, a small amount of carbon dioxide formed as a by-product in EB dehydrogenation is known to inhibit the catalytic activity of commercial catalyst due to the decomposition of active phase in the presence of carbon dioxide (*Appl. Catal.* 26, 65 (1986); *Appl. Catal.*, 67, 179 (1991)).

However, in the recent years, it has been disclosed that carbon dioxide may act in a positive manner in the dehydrogenation of ethylbenzene. Sugino et al. reported that the activity of dehydrogenation of ethylbenzene was significantly improved under the flow of carbon dioxide by means of a catalyst having an active carbon carrier impregnated with lithium ferrie. Sugino et al. reported that the source of the enhancement of activity was attributable to the oxidative dehydrogenation activity of ethylbenzene via carbon dioxide as an oxidant (*Appl. Catal.*, 121, 125 (1995)). Nozaki et al. observed that the enhancement effect of the dehydrogenation activity of ethylbenzene based on carbon dioxide under a $Na_2O/Al_2O_3$ basic catalyst. In latter case, it was explained that the enhancement of a catalytic activity was due to a shift in the reaction equilibrium towards styrene, attributable to the simultaneous occurrence of the dehydrogenation reaction of ethylbenzene and the reverse water-gas shift reaction which had the effect of converting hydrogen so produced by carbon dioxide (*Appl. Catal.*, 37, 207 (1988))

As explained above, various methods have been proposed in order to improve the dehydrogenation reaction of ethylbenzene with steam. In the case of the dehydrogenation reaction of ethylbenzene using carbon oxide, however, carbon dioxide works to deactivate the commercial catalyst therein. Consequently, in order to efficiently use carbon dioxide as a mild oxidant, it becomes necessary to design a new kind of catalyst which can promote the dehydrogenation reaction of ethylbenzene without decomposition of a catalyst by carbon dioxide.

SUMMARY OF THE INVENTION

The inventors herein have devised a new catalyst system which contains iron oxides for maintaining a high concentration of Fe(II) species on the surface of a zeolite, active carbon, γ-alumina or silica carrier. It was observed that the stability of a catalyst was markedly improved in addition to the enhancement of the dehydrogenation activity of ethylbenzene under carbon dioxide carrier gas as compared to that of the reaction condition without carbon dioxide. The improvement in the catalytic activity and stability under the present invention was due to the role of carbon dioxide. Further, the reaction activity was attributed to the fact that the initial state of a fresh catalyst has high concentration of Fe(II) species in iron oxide.

DETAILED DESCRIPTION OF THE INVENTION

The catalyst used in the present invention can be manufactured by the precipitation, impregnation, and sol-gel methods. As for the main point during the manufacturing process of a catalyst, the divalent iron metal salts as precursors should be used in order to increase the concentration of Fe(II) species on a catalyst. Alternatively, during the calcination and pretreatment of a catalyst, the catalyst should be manufactured after oxygen was removed therefrom. As for the example of the precipitation method of manufacturing the catalyst, a zeolite or other carriers were mixed at a certain concentration with a stable metal salt solution such as $FeSO_4$, $Fe(NO_3)_2$ with divalent oxidation state of iron. Thereafter, when the solution was adjusted to alkalinity at 60° C., the $Fe(OH)_2$ compound was precipitated on the carrier in the solution. Then, the precipitant was filtered, washed, dried and finally calcined. At this point, a 28% ammonia solution was used to adjust the pH to 11–12, and the precipitation, drying, and calcination processes were carried out under the flow of nitrogen or another inert carrier gas. The catalyst so manufactured under the aforementioned method can be expressed by the general formula (I) as follows:

$$(Fe^{II}_xFe^{III}_yO_z)/S \qquad (I)$$

In the above formula, S denotes a zeolite, active carbon, γ-alumina or silica carrier, and the initial condition of iron oxide is as follows:

$$x=0.1-2,\ x+y=3\ \text{and}\ z=(2x+3y)/2$$

In the examples of the present invention, the dehydrogenation reaction of aromatic hydrocarbons, i.e., ethylbenzene, was carried out in the continuous fixed-bed reaction system. The catalyst herein was placed in a tubular reactor, and the reaction was carried out by injecting the reactant, ethylbenzene, through the catalyst bed under the flow of carbon dioxide by means of the liquid injection pump. Ethylbenzene was injected by using a syringe pump, and the carbon dioxide gas passing through the mass flow controller was mixed with ethylbenzene, after which was pre-heated at 400° C. in a pre-heater for injection in the reactor. The reactor was made of quartz or stainless steel in 12 mm diameter. The reaction temperature was adjusted by an electric heater and a programmable temperature controller in the range of 500–700° C. The dehydrogenation catalyst so manufactured in 100 mesh size was placed in a reactor. Before the reaction, the catalyst was treated with nitrogen for 1 hour at 600° C. The molar ratio of carbon dioxide and ethylbenzene injected into the reactor may be in the range of 1:1 to 100:1. After the reaction, the reactants and products were analyzed by an on-lined gas chromatograph (Chrompack, Model CP 9001). At that point, with respect to the catalyst, the conversion of ethylbenzene and the yield of styrene were defined as follows:

Conversion of ethylbenzene (%)=[(A−B)/A]×100

Yield of styrene (%)=(C/A)×100, wherein A, B and C represent the concentrations of the following compounds, respectively:
A: Concentration of ethylbenzene so injected (wt %)
B: Concentration of remaining ethylbenzene after reaction (wt %)
C: Concentration of styrene produced after the reaction (wt %)

The invention herein is explained in more detail by the examples as below thout limitation thereby.

EXAMPLE 1

A catalyst supported by iron oxide/ZSM-5 zeolite used in the example herein as prepared by the precipitation method. The amounts of iron oxide in the examples were 1.5, 5, 10, 20, 50 wt %, respectively. The NaZSM-5 zeolite (Uetikon, Zeocat PZ/2–980) was used as a support for the iron oxide-supported catalyst. On the other hand, in order to measure the surface area of the solid sample, the adsorption analysis equipment (model ASAP 2400 of Micromeritics Co. of US) was used. At the temperature of liquid nitrogen, the surface area and the pore volume of the NaZSM-5 zeolite carrier, which was measured by physical adsorption of nitrogen under the BET method, were determined to be 388 $m^2/g$ and 0.222 ml/g, respectively.

The detailed preparation method of the catalyst is as follows: Before the preparation, nitrogen was flushed into the distilled water to remove oxygen therefrom, and an aqeuous $FeSO_4$ solution of 1 mole concentration was prepared. Into this solution, a ZSM-5 zeolite support at a certain concentration was mixed, and then a 28% ammonia solution was added therein to adjust the pH to 12 for the purpose of depositing the $Fe(OH)_2$ on the support. Under room temperatures, the precipitant was filtered and washed with distilled water in the ratio of 1 liter of distilled water to 100 g of the catalyst precursor, after which was dnred in a vacuum drying oven at 80° C. for 6 hours. At that point, the precipitation process was carried out in the inert gas flow without oxygen. Thereafter, the precipitant was calcined at 400° C. for 4 hours. The surface areas of the ZSM-5 zeolite-supported iron oxide catalysts according to the loading of iron oxide were as follows: 400 $m^2/g$ for 1.5 wt. % and 5 wt. % loading, 390 $m^2/g$ for 10 wt. % loading, 380 $m^2/g$ for 20 wt. % loading, 250 $m^2/g$ for 50 wt. % loading. Further, due to the high dispersion on the surface of the support, the structure of iron oxides in the catalysts could not be observed through the X-ray diffraction until the loading of iron oxide exceeded 10 wt. %. At the point of 20 wt. % and 50 wt. % loading, $Fe_3O_4$ in spinel phase having divalent and trivalent irons in co-existence was observed.

1 g of respective catalysts prepared by the aforementioned methods were placed in a tubular reactor. Then, the catalysts were treated with nitrogen at a flow rate of 100 ml/minute for an hour at 600° C. At the reaction temperature of 600° C., ethylbenzene was injected with the molar ratio of 30:1 with respect to carbon dioxide and ethylbenzene at a flow rate of 0.5 g/hour. The dehydrogenation activities. of the respective catalysts are shown in Table 1, which data were obtained after 4 hours followed by the reaction. Further, the catalytic activity in the case of use of nitrogen instead of carbon dioxide flux was measured and compared in Table 1. In all cases, the conversion of ethylbenzene and the yield of styrene obtained by means of carbon dioxide flux were markedly higher than those of the nitrogen flux. Based on such findings, the dehydrogenation activity with respect to ethylbenzene under a carbon dioxide flow was shown to increase as compared to the case of a nitrogen gas flow. On the other hand, the comparative results of catalystic activities obtained by means of a catalyst loaded with 5 wt. % of iron oxide on ZSM-5 zeolite (hereinafter No. 1 Catalyst) under a carbon dioxide or nitrogen flow are shown in Table 2.

TABLE 1

| | Carbon dioxide diluent | | Nitrogen diluent | |
| --- | --- | --- | --- | --- |
| Loading of iron oxides (wt. %) | Conversion of ethylbenzene (%) | Yield of styrene (%) | Conversion of ethylbenzene (%) | Yield of styrene (%) |
| 1.5 | 38 | 35 | 25 | 22 |
| 5 | 52 | 48 | 33 | 30 |
| 10 | 48 | 45 | 30 | 26 |
| 20 | 45 | 41 | 29 | 26 |
| 50 | 40 | 37 | 27 | 24 |

TABLE 2

| | | Carbon dioxide diluent | | Nitrogen diluent | |
| --- | --- | --- | --- | --- | --- |
| Type | Catalyst | Conversion of ethylbenzene (%) | Yield of Styrene (%) | Conversion of ethylbenzene (%) | Yield of Styrene (%) |
| Example 1 | No. 1 | 52 | 48 | 33 | 30 |
| Example 2 | No. 2 | 60 | 57 | 51 | 49 |
| Example 3 | No. 3 | 46 | 43 | 29 | 26 |
| Example 4 | No. 4 | 47 | 45 | 39 | 36 |
| Example 5 | No. 5 | 44 | 41 | 33 | 29 |
| Comp. Example 1 | No. 6 | 25 | 23 | 32 | 30 |
| Comp. Example 2 | No. 7 | 23 | 21 | 31 | 29 |
| Comp. Example 3 | No. 8 | 14 | 12 | 10 | 9 |
| Comp. Example 4 | No. 9 | 18 | 16 | 13 | 11 |

EXAMPLE 2

A catalyst in which 5 wt. % of iron oxides had been deposited onto the-active carbon (No. 2 Catalyst hereinafter) was manufactured by the same method of Example 1. Under the conditions of Example 1, the catalytic activities respectively using carbon dioxide and nitrogen as a dilution gas were measured and are shown in Table 2. A Darco active carbon (Batch 90.85) manufactured by Norit Co. of US was used as a support.

EXAMPLE 3

A catalyst in which 5 wt. % of iron oxide had been deposited onto the NaY zeolite carrier (No. 3 Catalyst hereinafter) was manufactured by the same method of Example 1. Under the conditions of Example 1, the catalytic activities respectively using carbon dioxide and nitrogen as a dilution gas were measured and are shown in Table 2. The carrier used herein was a NaY zeolite manufactured by Uetikon Co. (Zeocat Z6-01-01, surface area: 700 m²/g).

EXAMPLE 4

A catalyst in which 5 wt. % of iron oxide had been deposited onto the γ-alumina carrier (No. 4 Catalyst hereinafter) was prepared by the same method of Example 1. Under the conditions of Example 1, the catalytic activities respectively using carbon dioxide and nitrogen as a dilution gas were measured and are shown in Table 2. The carrier used herein was a γ-alumina carrier manufactured by Strem Chemical Co. (Strem 93-1329).

EXAMPLE 5

A catalyst in which 5 wt. % of iron oxide had been deposited onto the silica carrier (No. 5 Catalyst hereinafter) was prepared by the same method of Example 1. Under the conditions of Example 1, the catalytic activities respectively using carbon dioxide and nitrogen as a dilution gas were measured and are shown in Table 2. The carrier used herein was a silica carrier manufactured by Strem Chemical Co. (Strem 93-1435).

COMPARATIVE EXAMPLE 1

A K—$Fe_2O_3$ oxide was utilized herein, which had a similar composition to the commercial catalyst used in the dehydrogenation preocess of ethylbenzene via steam. In particular, $K_2CO_3$ solution was impregnated onto $Fe_2O_3$ oxides so that the composition was 77 wt % to 23 wt % with respect to $Fe_2O_3$ and $K_2CO_3$ (No. 6 Catalyst hereinafter). Thereafter, the catalyst was completed by calcination in air at 600° C. for 4 hours. Further, under the conditions of Example 1, the catalytic activities respectively using carbon dioxide and nitrogen as a dilution gas were measured and are shown in Table 2. In contrast to the catalyst in which iron oxide had been supported onto the zeolite or active carbon, the K—$Fe_2O_3$ oxides in the case of a carbon dioxide flow showed a significantly lower activity as compared to the case of a nitrogen flow.

COMPARATIVE EXAMPLE 2

An $Fe_3O_4$ oxide without a support (No. 7 Catalyst hereinafter) was prepared by the method of Example 1. Under the conditions of Example 1, the catalytic activities respectively using carbon dioxide and nitrogen as a dilution gas were measured and are shown in Table 2. In contrast to the catalyst in which iron oxides had been supported onto the zeolite or active carbon, the $Fe_3O_4$ oxide itself in the case of a carbon dioxide flow showed a significantly lower activity as compared to the case of a nitrogen flow.

COMPARATIVE EXAMPLE 3

The catalyst (No. 8 Catalyst hereinafter) was prepared by physically mixing the $Fe_3O_4$ oxide of Comparative Example 2 and the NaZSM-5 zeolite support used in Example 2 so that the concentration of $Fe_3O_4$ was 5 wt. %. Under the conditions of Example 1, the catalytic activities respectively using carbon dioxide and nitrogen as a dilution gas were measured and are shown in Table 2. In the case of physically mixing the $Fe_3O_4$ oxides and NaZSM-5 zeolite, the activity was significantly lowered as compared to those of No. 1 Catalyst of Example 1.

COMPARATIVE EXAMPLE 4

In order to compare the effects of iron oxides present in the zeolite carriers, the $Fe_2O_3$ oxide with only the trivalent oxidation state of iron on the NaZSM-5 zeolite of Example 1 was prepared by the impregnation method (hereinafter No. 9 Catalyst). In other words, the NaZSM-5 zeolite powder was mixed into 100 ml of the solution of 0.1 mole $Fe(NO_3)_3$ for 5 hours to the point of 5 wt. % of impregnation concentration. Then, the solution was transferred to a vacuum rotary evaporator for evaporation of water, after which was placed in an oven at 100° C. for 6 hours. Thereafter, the catalyst was completed by transferring it to the electric furnace for calcination at 600° C. for 4 hours. With respect to the catalysts so prepared, the activities for dehydrogenation of ethylbenzene are shown in Table 2. Since the activity of No. 9 Catalyst was markedly lower than that of No. 1 Catalyst, it was duly confirmed that the catalyst with abundant Fe(II) species in iron oxide increased the dehydrogenation activity of ethylbenzene in the presence of carbon dioxide.

EXAMPLE 6

With respect to No. 1 Catalyst of Example 1, the change in the catalytic activity was compared according to the reaction time under the same reaction condition of Example 1 when using dioxide and nitrogen as a dilution gas respectively. After 4 hours, the yields of styrene in the cases of use of carbon dioxide and nitrogen as dilution gas were 48% and 22%, respectively. After 20 hours, the yields of styrene were 47% and 3.9%, respectively. Under the flow of carbon dioxide, there was no change in catalytic activity with stability. However, under nitrogen dilution gas, the catalytic activity decreased 20% or more from the initial activity. Then, when the thermogravimetric analysis with the rising temperature under oxygen flow was used for the catalyst reacted under nitrogen diluent gas, it was confirmed that 0.85 g of coke was produced per 1 g of the catalyst therein. Consequently, a reduction of the catalytic activity under nitrogen diluent gas was determined to be caused by the large amount of coke which had the effect of blocking the adsorption of reactants from active sites of catalyst surface.

EXAMPLE 7

With respect to No. 1 Catalyst of Example 1, a change in the catalytic activities as shown in Table 3 in the cases where the reaction conditions of Example 1 were used except for the different pretreatment before the reaction. In particular, nitrogen, 5% hydrogen, carbon dioxide, or air, respectively, was flowed in at a rate of 50 ml/minute for 1 hour at 600° C. In the case of the nitrogen treatment, the catalytic activity was the highest while the lowest was observed in the case of air treatment. Based on the observation that the catalytic activities for air, hydrogen and carbon dioxide were lower than that of the nitrogen treatment, the optimum oxidation state of iron oxides for the catalyst was determined to be an oxide of a mixture of Fe(II) and Fe(III) species.

TABLE 3

| Pre-treatment gas | Carbon dioxide diluent | | Nitrogen diluent | |
| --- | --- | --- | --- | --- |
| | Conversion of ethylbenzene (%) | Yield of styrene (%) | Conversion of ethylbenzene (%) | Yield of styrene (%) |
| Nitrogen | 52 | 48 | 33 | 30 |
| 5% hydrogen | 38 | 35 | 30 | 28 |
| Carbon dioxide | 40 | 36 | 29 | 27 |
| Air | 28 | 26 | 21 | 19 |

What is claimed is:

1. A method of dehydrogenation of aromatic hydrocarbons, which comprises: contacting the aromatic hydrocarbons with a catalyst having the following formula (I) under the flow of carbon dioxide as a dilution gas and at a temperature ranging from 500° C. to 700° C.

$$(Fe^{II}_x Fe^{III}_y O_z)/S \qquad (I)$$

wherein x is a number between 0.1 and 2, x+y=3, and z=(2x+3y)/2, and S is a support for the catalyst.

2. The method of claim 1, wherein the molar ratio of carbon dioxide to the aromatic hydrocarbons is in the range of 1:1 to 100:1.

* * * * *